(12) United States Patent
Nekovar et al.

(10) Patent No.: US 11,564,643 B2
(45) Date of Patent: Jan. 31, 2023

(54) MONITORING HANDLING OF AN OBJECT

(71) Applicant: Siemens Healthcare GmbH, Erlangen (DE)

(72) Inventors: Anton Nekovar, Neunkirchen (DE); Mohammad Sharifi, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 338 days.

(21) Appl. No.: 16/868,261

(22) Filed: May 6, 2020

(65) Prior Publication Data
US 2020/0359976 A1    Nov. 19, 2020

(30) Foreign Application Priority Data
May 14, 2019 (DE) .......................... 102019206960.6

(51) Int. Cl.
| | |
|---|---|
| *G06T 7/00* | (2017.01) |
| *A61B 6/06* | (2006.01) |
| *G06T 7/246* | (2017.01) |
| *G06T 1/00* | (2006.01) |
| *A61B 6/00* | (2006.01) |
| *A61B 6/12* | (2006.01) |

(52) U.S. Cl.
CPC .............. *A61B 6/06* (2013.01); *A61B 6/12* (2013.01); *A61B 6/541* (2013.01); *G06T 1/0014* (2013.01); *G06T 7/251* (2017.01); *G06T 2207/10116* (2013.01); *G06T 2207/30016* (2013.01); *G06T 2207/30041* (2013.01)

(58) Field of Classification Search
CPC ..................................................... A61B 6/541
See application file for complete search history.

(56) References Cited

U.S. PATENT DOCUMENTS

| | | | |
|---|---|---|---|
| 5,278,887 A | 1/1994 | Chiu et al. | |
| 8,754,388 B2 | 6/2014 | Guez | |
| 2015/0078523 A1* | 3/2015 | Melman ............... | A61B 6/4028 378/62 |
| 2018/0129896 A1 | 5/2018 | Wu | |

OTHER PUBLICATIONS

German Office Action for German Application No. 10 2019 206 960.6 dated Feb. 6, 2020.

\* cited by examiner

*Primary Examiner* — Dani Fox
(74) *Attorney, Agent, or Firm* — Lempia Summerfield Katz LLC

(57) ABSTRACT

In order to reduce a radiation dose delivered to an object or an observer, a facility for monitoring handling of the object has an optical unit configured to direct ionizing radiation onto the object and also a filter element in order to attenuate a part of the ionizing radiation. An imaging unit may detect portions of the ionizing radiation passing through the object in order to create an image of the object. A view acquisition system may acquire a viewing movement, and a control unit is configured, during a first operating mode, to control a position of the filter element as a function of the viewing movement. The control unit is configured to identify a predefined sequence of viewing movements and, as a function thereof, to switch into a second operating mode. The position of the filter element is controlled during the second operating mode as a function of an image analysis.

16 Claims, 3 Drawing Sheets

MONITORING HANDLING OF AN OBJECT

The present patent document claims the benefit of German Patent Application No. 10 2019 206 960.6, filed May 14, 2019, which is hereby incorporated by reference.

TECHNICAL FIELD

The present disclosure relates to a facility for monitoring handling of an object, which has an optical unit configured to direct ionizing radiation onto the object. The facility also has a filter element that may be arranged in a beam path of the ionizing radiation and is configured to attenuate part of the ionizing radiation. The facility further includes an imaging unit configured to detect portions of the ionizing radiation passing through the object in order to create an image of a part of the object. The facility further includes a view acquisition system configured to acquire a viewing movement of an observer. Additionally, the facility has a control unit, which is configured, during a first operating mode, to control a position of the filter element as a function of the viewing movement. The disclosure further relates to a training facility for a model for image analysis when monitoring handling of an object, a method for training a model for image analysis when monitoring handling of an object, a method for monitoring handling of an object, a computer program, and a computer-readable storage medium.

BACKGROUND

During handling of an object, which is supported by ionizing radiation, (e.g., during x-ray-assisted catheter guidance during a therapeutic intervention on a patient or a non-medical intervention on another object), it may be of advantage for the dose of ionizing radiation to which an observer, (e.g., a doctor and/or the object), is subjected, to be as small as possible. To this end, a filter element may be introduced into the beam path of the ionizing radiation, which defines a priority region within which the ionizing radiation is not to be attenuated in order to achieve as good imaging results as possible and outside of which priority region the ionizing radiation is attenuated. Because the position of a Region of Interest (ROI), which is to be imaged with the highest possible image quality, may change during the handling, the position of the filter element may be controlled accordingly.

If the position of the filter element is controlled as a function of a viewing movement of the observer by a view acquisition system, then the view acquisition system may lose a current viewing position of the user or the observer, e.g., cannot or cannot correctly acquire the viewing movement, or for other reasons it is not possible to position the filter element correctly. In such a case, the filter element may be removed completely from the beam path, for example, in order to guarantee that the ROI continues to be imaged with good image quality.

The disadvantage is that this causes the actual function of the filter element, namely the reduction in dose for the observer and/or object, to be lost. A further disadvantage is that the removal of the filter element as well as the reintroduction of the filter element into the beam path may lead to disruptive artifacts in the imaging.

Described in U.S. Pat. No. 5,278,887 are a facility and a method for reducing the x-ray dose during a fluorescence-assisted method. In this disclosure, a filter element is employed that lets x-ray radiation pass through it without any attenuation in order to image a region of interest with high x-ray intensity and a correspondingly high image quality.

Described in U.S. Pat. No. 8,754,388 B2 is a system for radiation control in order to minimize radiation delivered to a patient or to a user of the system. To this end, an attention monitoring system is employed, which may be embodied as a brain sensor system or as an eye sensor system. A region of interest is automatically determined based on the attention monitoring system.

SUMMARY AND DESCRIPTION

The scope of the present disclosure is defined solely by the appended claims and is not affected to any degree by the statements within this summary. The present embodiments may obviate one or more of the drawbacks or limitations in the related art.

An object of the present disclosure is to specify an improved concept for monitoring handling of an object while using ionizing radiation, wherein a dose of ionizing radiation delivered to the object and/or an observer may be reduced.

In accordance with the disclosure, this object is achieved by a facility for monitoring handling of an object, by a training facility for a model for image analysis when monitoring handling of an object, by a method for training of a model for image analysis when monitoring handling of an object, by a method for monitoring handling of an object, by a computer program, and a computer-readable storage medium.

The improved concept is based on the idea of controlling a position of a priority region as a function of the viewing movement of the observer during an operating mode and, when a defined sequence of viewing movements of the observer is detected, of controlling the position of the priority region as a function of an image analysis or leaving it unchanged.

In accordance with a first independent aspect of the improved concept, a facility for monitoring handling of an object is specified. The facility has an optical unit, which is configured to direct ionizing radiation, (e.g., x-ray radiation), onto the object. Moreover, the facility has a filter element, an imaging unit, a view acquisition system, and a control unit. The filter element, which is arranged in particular in or on the optical unit, may be brought into a beam path of the ionizing radiation or be arranged in the beam path in order to attenuate a part of the ionizing radiation, in particular an intensity of the part of the ionizing radiation, in particular in order to define a priority region. The imaging unit is configured to detect portions of the ionizing radiation passing through the object in order to create an image of a part or a region of the object. The view acquisition system is configured to acquire a viewing movement of an observer, in particular of an observer of the image or of a representation of the image, (e.g., on a visual display unit).

The control unit, which in particular is coupled to the view acquisition system, is configured to obtain viewing movement data created by the view acquisition system, (e.g., based on the acquisition of the viewing movement), during a first operating mode, (e.g., of the facility and/or the control unit). The viewing movement data is obtained to control a position of the filter element as a function of the viewing movement, in particular of the viewing movement data, in particular in order to control a position of the priority region. The control unit is configured, as a function of the viewing movement, to identify a predefined sequence of viewing movements, (e.g., of the observer). The control unit is also configured to switch from the first operating mode into a second operating mode, (e.g., of the facility or of the control unit), when the sequence of viewing movements has been identified. The control unit is configured to control the position of the filter element during the second operating mode as a function of an image analysis of the image, (e.g., a result of the image analysis), or to leave the position of the filter element unchanged during the second operating mode.

The handling of the object may involve handling with the aid of a tool. In the case of medical treatment of a patient, the tool may involve a catheter. The part of the object of which the image is obtained by the imaging unit contains the tool or a specific region of the tool for example, (e.g., a catheter tip of the catheter). Controlling the position of the filter element during the first or the second operating mode may serve to follow the tool or the specific region of the tool during the handling, so that the observer may provide themselves with a precise picture of the position of the tool, in particular within the object, (e.g., within a patient's body).

The optical unit may receive the ionizing radiation from a radiation source, which is optionally contained in the facility.

The filter element attenuates the part of the ionizing radiation when it is arranged in the beam path in order to keep the dose of ionizing radiation delivered to an observer and/or to the object as low as possible. A further part of the ionizing radiation is not attenuated by the filter element or is only attenuated very much less than the part of the ionizing radiation. The further part of the radiation may thus strike the object essentially unattenuated, so that the image of the part of the object may be created with the highest possible image quality, in particular, with a low noise component. The priority region in particular involves that region of the object or on the object that the further part of the ionizing radiation essentially strikes unattenuated.

The tool, the marked region of the tool, or a region of the object within which the tool or the marked region of the tool is located, corresponds to a Region of Interest (ROI), because the marked region of the tool, (e.g., the catheter tip), involves that part that the observer has to keep in view if possible in order to be able to carry out the handling of the object by the tool, in particular to be able to guide the tool as precisely as possible. Because the ROI may move during the handling with the tool, (e.g., as a result of a corresponding movement of the tool and/or of the object), the priority region may be controlled in such a way that it matches the ROI as closely as possible or lies within the ROI or the ROI lies within the priority region, so that the ROI is imaged with the highest possible quality.

The control unit is accordingly coupled to the view acquisition system and to the imaging unit, for example, and also in particular to the filter element and/or the optical unit. The facility, (e.g., the optical unit of the facility), may include a drive system for moving the filter element in order to move the position of the filter element as a function of control signals that are generated by the control unit for control of the filter element.

The observer may be a person who is carrying out the handling of the object by the tool, (e.g., a doctor). The observer may thus be a user of the facility. However, the observer may also be a further person, who is observing the handling of the object and is not necessarily carrying it out himself. For example, the observer may be a member of the medical staff or technical staff.

The view acquisition system may contain an eye tracker or be embodied as an eye tracker, for example. The eye tracker may be accommodated in or on eyeglasses or another such device that the observer may wear, or may be arranged as a stationary device in the observer's environment. The eye tracker may create view acquisition data or eye tracker data by active optical sensors and/or cameras as a function of the viewing movement of the observer.

The image in particular contains image data, which is created by the imaging unit as a function of portions of the ionizing radiation passing through the object in order to be able to represent the object and/or the tool visually for the observer. The image data may be displayed as a visual image or visual representation on the visual display unit. Furthermore, the image data may be analyzed accordingly by the image analysis, for example, in order to identify where the presumed ROI is located in order to be able to control the filter element accordingly as a function thereof.

The control unit is configured in particular to acquire the viewing movement repeatedly, to compare the repeatedly acquired viewing movement with the predefined sequence of viewing movements, and to identify the predefined sequence of viewing movements based on a result of the comparison.

The identification of the predefined sequence of viewing movements may be understood such that it is established by the control unit that the repeatedly acquired viewing movement corresponds to the predefined sequence of viewing movements.

The identification of the predefined sequence of viewing movements as a function of the viewing movement of the observer may include the fact that the viewing movement is continuously or repeatedly acquired or monitored and correspondingly continuously or repeatedly compared with the predefined sequence of viewing movements, e.g., at least one predefined reference viewing movement or a predefined sequence of predefined reference viewing movements, which in particular may be stored on a storage medium of the facility. In order to do this, the control unit makes use of the view acquisition data of the view acquisition system for example.

If the control unit establishes by the comparison that a sequence of viewing movements of the observer, in particular up to a predetermined tolerance, matches the predefined sequence of viewing movements, it has accordingly identified the sequence of viewing movements and may switch itself or the facility from the first into the second operating mode.

During the first operating mode, the view acquisition system in particular detects a view of the observer or the viewing movement. The view of the observer is in particular directed to a visual display unit, (e.g., a monitor), on which the image is being shown.

During the first operating mode, the control unit may identify a direction of view of the observer based on the view acquisition data. Accordingly, it may be assumed from this that the direction of view is directed to the ROI. Therefore, during the first operating mode, the position of the priority region or the position of the filter element is controlled in such a way that the priority region matches a region around a point to which the view of the observer is directed. In particular, the priority region may be imaged by the image in such a way that the direction of view of the observer is directed to the image of the priority region, in particular, that a center of the image of the priority region matches a point to which the view of the observer is directed, (e.g., a fixation point). What may be achieved by controlling the priority region corresponding to the direction of view of the observer during the first operating mode is that the priority region corresponds to the ROI where possible, which is thereby imaged with the highest possible quality.

The sequence of viewing movements may correspond to a sequence of viewing movements of the observer, which indicate or allow it to be concluded that the view of the observer is being moved in a predefined way away from the ROI, in particular from the image of the ROI, in particular on the visual display unit. This may correspond to a situation in which the view of the observer is directed away from the visual display unit to a further display, for example, in an environment of the visual display unit, in particular briefly and/or temporarily. Information of relevance for the handling of the object may be shown on the further visual display unit, (e.g., an EKG in the case of a medical procedure, a reference image, a pulse graph, or an oxygen saturation range or the like). It may also involve a situation in which the observer directs their view explicitly and intentionally to the object and/or the tool, (e.g., a position of the catheter or of the catheter tip), in order in particular cases to guide it by direct observation of the tool instead of an indirect observation of the tool via the image.

If the sequence of viewing movements has been identified, then depending on the acquisition area of the view acquisition system, the view acquisition system may still be in a position to acquire the viewing movements of the observer. In other situations, the view acquisition system may no longer acquire the viewing movements of the observer in this case because, according to the sequence of viewing movements, the view of the observer has moved out of an acquisition area of the view acquisition system.

During the second operating mode by the image analysis of the image, a region of the tool or a marked region of the tool, (e.g., the catheter tip), may be detected in the image, such as in image data that defines the image. The control unit may access a model, which may be present in the form of an algorithm, (e.g., a software algorithm), or in the form of a computer program, which is stored on the storage medium and may access and execute the model in order to detect the position of the region of the tool from the image or in the image. The model may involve a trained model.

If the region of the tool has been detected from the image data, the control unit may control the filter element in such a way that the priority region is imaged to a region around the marked region of the tool. Accordingly, it is assumed that the marked region of the tool corresponds to the ROI or lies within the ROI, in particular in the center of the ROI.

By the image analysis and the corresponding control of the image element, this enables a redundancy to be created for the control of the filter element based on the viewing movements of the observer.

As an alternative to control based on the image analysis, the control unit may leave the position of the filter element unchanged during the second operating mode, e.g., not control the filter element and in particular not remove the filter element from the beam path.

By a facility according to the improved concept, the radiation dose may be reduced for the object and the observer on the one hand by the filter element being provided in order to attenuate part of the ionizing radiation. The dose is reduced further however by the filter element being able to be arranged in the beam path of the ionizing radiation both in the first operating mode and also in the second operating mode, (e.g., regardless of whether or not the view acquisition system may acquire the view of the observer and regardless of whether or not the position of the filter element is controlled as a function of the viewing movement).

In particular, the filter element remains arranged in the beam path in the first and the second operating mode. A removal of the filter element from the beam path with the objective of continuing to be able to image the ROI with the highest possible image quality is no longer necessary in accordance with the improved concept.

In particular, the priority region also remains correctly positioned during the second operating mode and correlated with the ROI or with the presumed ROI, because the control in the second operating mode may be carried out based on the image analysis results.

The fact that the predetermined sequence of viewing movements has been identified enables it to be assumed that a removal of the filter element is not required in order to continue to guarantee a good imaging and image quality of the ROI.

Because the moving of the filter element out of the beam path would significantly increase the dose for object and/or observer, this contributes to a reduction in dose.

A further advantage is that a further observer, who in particular continues to keep the ROI in view, in particular while the observer may be looking at another visual display unit or at a catheter, may still see the ROI correctly positioned with high image quality when the position of the filter element is controlled based on the image analysis. Moreover, the priority region then also remains correctly positioned without any delay even during a switch from the second operating mode into the first operating mode, because the filter element does not first have to be moved back into the beam path again.

Moreover, disruptive artifacts through the movement of the filter element into and out of the beam path are avoided for the observer.

Even with a malfunction of the view acquisition system, (e.g., if the view acquisition system loses the view of the observer or incorrectly identifies the predefined sequence of viewing movements and accordingly switches to the second operating mode, but the observer may still have their view directed to the ROI), the region remains recognizable with good image quality because of the control of the filter element as a result the image analysis.

The control unit may be configured, in the second operating mode, to control the position of the filter element as a function of an image analysis of the image, regardless of the reason for which the switch to the second operating mode has been made. In particular, as well as the identification of the predefined sequence of viewing movements, there may also be other criteria or situations that cause the control unit to switch into the second operating mode.

In accordance with at least one form of embodiment of the facility for monitoring the handling of the object, the optical unit contains a collimator facility in order to convert the ionizing radiation at least partly into a parallel bundle of rays, e.g., to parallelize it. In particular, the filter element, when it is located in the beam path, is arranged between the collimator facility and the object.

In this way, a more specific and more precise definition of the priority region may be made possible.

In accordance with at least one form of embodiment, the control unit is configured to control the position of the filter element as a function of the viewing movement whenever the control unit and/or the facility are in the first operating mode.

In accordance with at least one form of embodiment, the facility contains a visual display unit, wherein the imaging unit is coupled to the visual display unit in order to transmit the image data or the image or other data representing the image to the visual display unit, in order to make possible a visual representation of the image on the visual display unit, which may include a monitor or display.

In accordance with at least one form of embodiment, the control unit is configured to control the position of the filter element as a function of the image analysis of the image whenever the control unit and/or the facility are in the second operating mode.

In accordance with at least one form of embodiment, the control unit is configured to recognize as a function of the viewing movement whether the direction of view of the observer lies within a predetermined view direction area. The control unit is configured to retain the first operating mode or to switch from the second operating mode into the first operating mode if the direction of view lies within the view direction area.

In the first operating mode, the filter element is then controlled again in particular based on the viewing movement of the observer.

The view direction area may correspond to a view of the observer, which is directed to the visual display unit.

What this achieves is that, if possible, the first operating mode is activated, in particular after the second operating mode has been activated and the first operating mode may be activated again. Depending on the training state or other characteristics of the model for image analysis or other individual case circumstances, the identification of the ROI by the view acquisition system may be more reliable or more precise than the identification of the ROI based on the image analysis.

In accordance with at least one form of embodiment, the control unit is configured to remove the filter element from the beam path of the ionizing radiation when the second operating mode was activated for at least a predetermined maximum duration, in particular when the position of the filter element is left unchanged during the second operating mode.

The maximum duration may lie in the range of 1 s to 10 s, (e.g., 3 s to 7 s or approximately 5 s).

This enables that, in the event of an incorrect or undesired activation of the second operating mode, the ROI may not be displayed with non-optimum image quality for any length of time.

In accordance with at least one form of embodiment, the control unit is configured to switch from the second operating mode into the first operating mode when the second operating mode was activated for a predetermined period of time, in particular continuously or uninterrupted.

In accordance with at least one form of embodiment, it is detected from the identification of the sequence of viewing movements that the direction of view of the observer or the view of the observer lies within a predetermined further view direction area.

The further view direction area may correspond to the observer viewing a further visual display unit. In particular, it is not the image that was created by the imaging unit that is displayed on the further visual display unit but further information relevant to the handling of the object, for example.

In particular, the observer may, if the sequence of viewing movements has been identified, direct their view intentionally and may briefly or temporarily direct their view to the further visual display unit in order to acquire the further information, and for example thereafter direct their view back to the visual display unit, in particular, to the ROI.

In particular, in such a situation it would be especially undesirable for the filter element to be removed from the beam path in order to insure the high image quality of the ROI, because in such a case the observer is not actually looking at the ROI at all.

In accordance with at least one form of embodiment, the facility includes the further visual display unit.

In accordance with at least one form of embodiment, the control unit is configured to switch from the first operating mode into the second operating mode when the view acquisition system cannot acquire the viewing movement of the observer.

The view acquisition system, because of an error of the view acquisition system or a fault of the view acquisition, (e.g., when a further object is located between the view acquisition system and the observer), may lead to the view acquisition system losing visual contact with the observer. For example, the view acquisition system also cannot acquire the viewing movement of the observer when the view of the observer no longer lies in the acquisition area of the view acquisition system.

In particular, in such a case, a switch is made into the second operating mode, although in this case the sequence of viewing movements is not necessarily being detected.

Also, in the case of an error or for another reason that leads to the view acquisition system no longer acquiring the viewing movement of the observer, in the second operating mode, the position of the filter element is accordingly controlled based on the image analysis, so that here too the filter element advantageously does not have to be removed from the beam path in order to guarantee a continuing high image quality, in particular of the ROI.

In accordance with at least one form of embodiment, the facility includes a processing unit, in particular coupled to the control unit and the imaging unit, which is configured to carry out the image analysis in order to determine the position of the ROI. The control unit is configured to control the position of the filter element during the second operating mode as a function of the position of the ROI.

As described above, it may be assumed that during the first operating mode the ROI coincides or in any event partly coincides with a region of the representation of the image on the visual display unit to which the view of the observer is directed. In the second operating mode, it may be assumed that the ROI corresponds to the marked region of the tool.

Thus, based on the image analysis, a position of the marked region of the tool is established and defined as the target position for the priority region in order to control the filter element by the control unit in such a way that the priority region matches the marked region of the tool, e.g., the presumed ROI.

In accordance with at least one form of embodiment, the control unit is configured, as a function of the viewing movement, to identify a predefined further sequence of viewing movements. The control unit is configured to determine at least one status variable of the facility and/or a change to the at least one status variable. The control unit is configured, depending on the at least one status variable or on a change to the at least one status variable, to switch from the first operating mode into a second operating mode when the further sequence of viewing movements has been identified.

As explained above, the sequence of viewing movements may correspond to a situation in which the observer intentionally briefly looks away from the visual display unit and when this may be established with corresponding reliability based solely on the identified sequence of viewing movements.

If the further sequence of viewing movements is identified, the situation may be the same. However, it may be assumed with sufficient likelihood that the observer is only looking away from the visual display unit briefly and temporarily. Therefore, the status variable of the facility may be included additionally in order to decide whether a switch is to be made into the second operating mode.

The latter may correspond to a situation in which the observer is looking at an operating element to change the status variable in order thereafter to look back again at the visual display unit. In accordance with such forms of embodiment, the unnecessary moving out of the filter element may thus be avoided here too.

In accordance with at least one form of embodiment, the at least one status variable contains a relative position and/or a relative orientation of one component of the facility with regard to a further component of the facility.

In accordance with at least one form of embodiment, the at least one status variable contains relative position and/or a relative orientation of at least one component of the facility with regard to the object or the tool.

The components may correspond to the optical unit or the imaging unit, for example.

In accordance with at least one form of embodiment, the at least one status variable contains an operating parameter for operating the facility, (e.g., the radiation source, the optical unit, the filter element, the imaging unit, the view acquisition system, or the control unit).

In accordance with at least one form of embodiment, the at least one status variable contains a distance between the radiation source and the imaging unit, in particular a Source-to-Image Distance (SID).

In accordance with at least one form of embodiment, the at least one status variable contains an angulation of the facility, wherein the facility is designed in particular as a C-arm device.

In accordance with at least one form of embodiment, the facility contains a camera system, which is configured to create camera data that images the observer. The control unit is configured, depending on the camera data, and for example depending on the at least one status variable or on a change to the at least one status variable, to switch from the first operating mode into a second operating mode when the further sequence of viewing movements has been identified.

The control unit or the processing unit may be configured to determine, based on the camera data, a position or pose of the observer or of a part of the observer's body, for example the observer's head, in relation to the facility. The control unit may then switch into the second operating mode depending on this information.

In accordance with a further independent aspect of the improved concept, a training facility for a model for image analysis when monitoring handling of an object is specified, wherein the training facility has an optical unit configured to direct ionizing radiation onto the object. The training facility has a filter element, which may be arranged in a beam path of the ionizing radiation in order to attenuate a part of the ionizing radiation and thereby to define a priority region as well an imaging unit configured to detect portions of the ionizing radiation passing through the object in order to create an image of a part of the object. The training facility has a view acquisition system configured to acquire a viewing movement of an observer and also a control unit configured to determine a target position for the priority region as a function of the viewing movement. The training facility has a processing unit configured to determine a parameter set for the model based on a correlation of the image with the target position.

The model, in particular the parameter set determined, may be used by a facility for monitoring handling of an object, in particular by its control unit and/or processing unit in order to control the position of the filter element based on the image analysis, in particular in order to carry out the image analysis.

Further forms of embodiment of the training facility follow on directly from the various forms of embodiment of the facility for monitoring handling of the object and vice versa.

The training facility may physically involve the same facility as the facility for monitoring handling of an object.

In accordance with a further independent aspect of the improved concept, a method for training a model for image analysis when monitoring handling of an object is specified. In accordance with the method, ionizing radiation is directed onto the object. A part of the ionizing radiation is attenuated, in particular by a filter element, which may be introduced into the beam path of the ionizing radiation in order to define a priority region. An image of a part of the object is created based on portions of the ionizing radiation passing through the object, in particular by an imaging unit. A viewing movement is acquired of an observer, in particular of an observer of the image on a visual display unit, in particular by a view acquisition system. A target position for the priority region is determined as a function of the viewing movement, in particular by a control unit. A parameter set for the model for image analysis, in particular for analysis of the image, is determined based on a correlation or a comparison of the image, in particular of the image data, with the target position, in particular by a processing unit control unit.

The filter element may be controlled by the control unit according to the target position, so that the priority region is moved to the target position.

The model serves during a run time, e.g., during the carrying out of a method for monitoring handling of the object, in particular to establish the target position based on the analysis of the image and to predetermine it as the target position for the priority region for control of the filter element. During the training method, the target position is however predetermined independently of the model, e.g., by an external source, in that the target position is derived from the viewing movement of the observer. What is involved here in particular is supervised learning, in particular supervised machine learning, with which the model is trained in a method for training the model.

The parameter set determined may be seen as a result of the method for training the model. The parameter set may then be used at run time for productive or actual image analysis of the image and accordingly to determine the target position for the priority region.

The described acts of the method for training the model may be carried out repeatedly or iteratively, in particular until the parameter set corresponds to predetermined quality criteria, e.g., the model may determine the target position based on the current parameter set with predetermined precision. In each iteration, the image of the object may be changed, (e.g., by a tool), which is used for handling of the object and may be located within the object. This enables a plurality of training datasets to be created, by which the model may be trained iteratively.

In particular, the model serves to identify from a given image the position of the marked region of the tool. In this case, it is assumed that the observer is directing their view to the marked region of the tool in the image on the visual display unit.

An advantage of the method for training the model lies in the fact that the view acquisition system may create a large amount of training data of high quality. This makes an effective training of the model possible.

The method for training the model may be undertaken in particular online, meaning that the training data is acquired at run time, e.g., during actual monitoring of the handling of an object. During the run time, the position of the filter element or the position of the priority region may be controlled based on the target position, which was determined as a function of the viewing movement. The training itself, e.g., the correlation or the comparison of the image or of the image data with the respective target position, may likewise be undertaken online, e.g., during run time, or later after conclusion of the monitoring.

Online training enables inherent system, application and user-specific, e.g., observer-specific, influences also to be taken into consideration in detail, which leads to a high quality of training.

The processing unit may have software elements and/or hardware elements, (e.g., a microprocessor). The processing unit may be embodied as a computer or as part of a computer system.

In accordance with at least one form of embodiment of the method for training the model, a further target position is determined based on the model using the parameter set determined based on the image, in particular by the processing unit. The further target position is compared with the target position, in particular by the processing unit, and quality code for the parameter set determined is defined based on a result of the comparison of the target position with the further target position, in particular by the processing unit.

In such a form of embodiment, a productive application of the model by the parameter set determined is tested, in that the further target position is determined by testing based on the image by the image analysis.

The quality code may quantify a deviation of the target position from the further target position and thus express how well the model may determine the target position, using the parameter set being used at the time, based on the image analysis.

The acts for training the model are in particular repeated iteratively until the quality code corresponds to a predetermined quality value or lies within a predetermined range for the quality code.

Further forms of embodiment of the method for training the model follow on directly from the various forms of embodiment of the facility for monitoring the handling of the object and the training facility and vice versa in each case. In particular, the training facility according to the improved concept is configured or programmed to carry out a method for training according to the improved concept or the training facility carries out a method for training according to the improved concept.

In accordance with at least one form of embodiment of the facility for monitoring handling of an object, the control unit is configured to control the position of the priority region during the second operating mode based on a trained model, wherein the model has been trained as a function of control data that was created during the first operating mode in order to control the position of the priority region as a function of the viewing movement. In particular, the model has been trained based on a method for training a model for image analysis when monitoring handling of an object according to the improved concept.

In accordance with a further independent aspect of the improved concept, a method for monitoring handling of an object is specified, wherein ionizing radiation is directed, in particular by an optical unit, onto the object. A part of the ionizing radiation is attenuated, in particular by a filter element in order to define a priority region. An image of a part of the object is created based on portions of the ionizing radiation passing through the object, in particular by an imaging unit. A viewing movement of an observer, in particular of the image is acquired, in particular by a view acquisition system.

During a first operating mode, in particular of the monitoring, a position of the priority region is controlled as a function of the viewing movement, in particular by a control unit. Depending on the viewing movement, a predefined sequence of viewing movements is identified, in particular by the control unit. A switch is made from the first operating mode into a second operating mode, in particular by the control unit, when the sequence of viewing movements has been identified. The position of the priority region is controlled during the second operating mode, in particular by the control unit, as a function of an image analysis of the image.

The controlling of the priority region in this case corresponds to the controlling of the filter element.

In accordance with at least one form of embodiment of the method for monitoring the handling of the object, for controlling the position of the priority region as a function of the viewing movement, in particular during the first operating mode, a target position for the priority region is determined as a function of the viewing movement, in particular by the control unit. A position of the filter element for attenuating the part of the radiation is controlled in such a way that the position of the priority region matches the target position at least approximately.

In accordance with at least one form of embodiment of the method for monitoring, the position of the priority region is controlled during the second operating mode based on a trained model. The model is trained as a function of control data, in particular by a processing unit, wherein the control data is created during the first operating mode in order to control the position of the priority region as a function of the viewing movement, in particular by the control unit.

The training of the model as a function of the control data may be undertaken as a function of the target position for the priority region. The training may be carried out by correlation of the target position with image data of the image.

The training may include a comparison of the target position with a target training position, wherein the target training position is established by the processing unit as a function of the image data.

In accordance with at least one form of embodiment of the method for monitoring the handling of the object, the model is trained by a method for training a model for image analysis according to the improved concept.

In accordance with at least one form of embodiment of the method for monitoring, a position of the ROI is determined or estimated by the image analysis. The position of the ROI is defined as the further target position for the priority region in order to control the position of the priority region during the second operating mode.

In particular, to determine the further target position, a position of the region of the tool in the image data is identified and determined. The position of the filter element is then controlled in such a way that the position of the priority region corresponds to the further target position.

In accordance with at least one form of embodiment of the method for monitoring, it is determined as a function of the viewing movement whether a direction of view of the observer lies within a predetermined view direction area. When the direction of view lies within the view direction area, the first operating mode is retained, or a switch is made from the second operating mode into the first operating mode.

In accordance with at least one form of embodiment of the method for monitoring, it is recognized through the identification of the sequence of viewing movements whether or that the direction of view of the observer lies within a predetermined further view direction area.

Further forms of embodiment of the method for monitoring the handling of the object according to the improved concept and vice versa follow on directly from the various forms of embodiment of the facility. In particular, a facility according to the improved concept may be configured or programmed to carry out a method for monitoring according to the improved concept, or the facility carries out such a method.

In accordance with a further independent aspect of the improved concept, a computer program with instructions is specified, wherein the instructions, when the computer program is executed by a facility according to the improved concept, in particular by a processing unit of the facility, cause the facility to carry out a method for training the model for image analysis according to the improved concept and/or a method for monitoring the handling of the object.

In accordance with a further independent aspect of the improved concept, a computer-readable storage medium is specified on which a computer program according to the improved concept is stored.

BRIEF DESCRIPTION OF THE DRAWINGS

The disclosure will be explained below in greater detail based on concrete exemplary embodiments and associated schematic drawings. In the figures, the same elements or elements with the same functions are provided with the same reference characters. It may be that the description of elements that are the same or have the same functions is not necessarily repeated in different figures.

In the figures.

DETAILED DESCRIPTION

Figure 1:
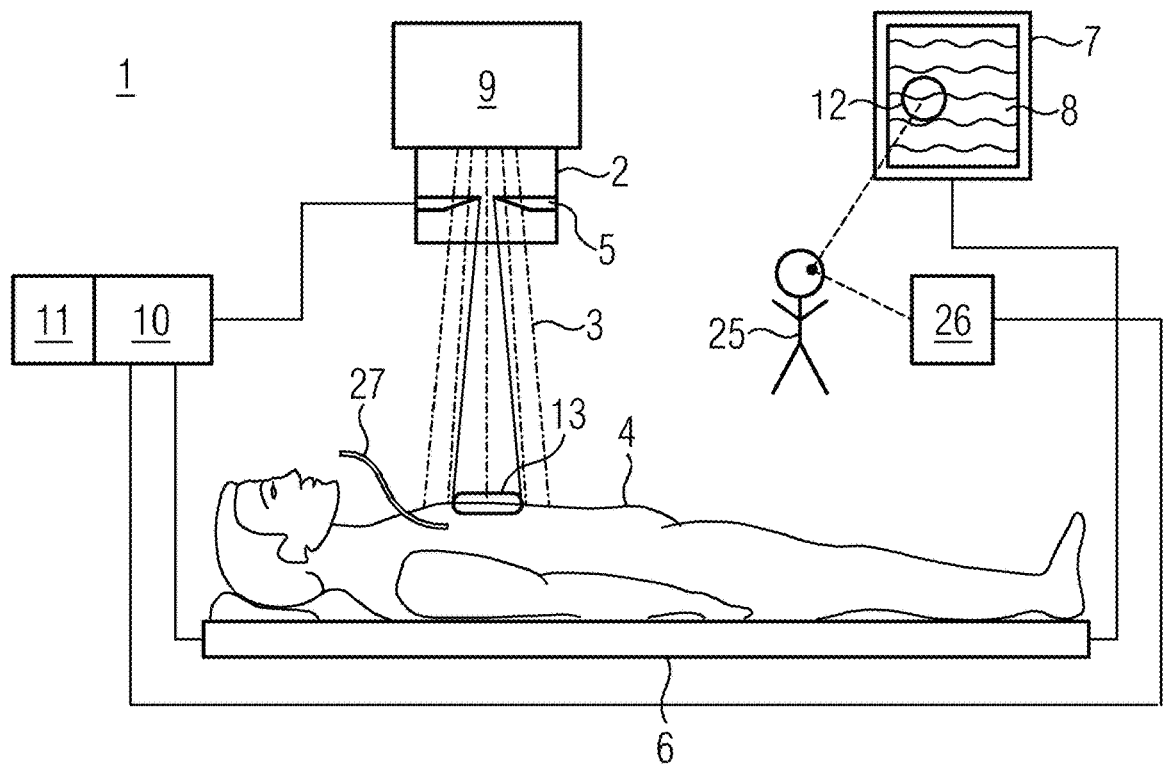
FIG. 1 depicts a schematic diagram of an example of a form of embodiment of a facility according to the improved concept.

Shown in FIG. 1 is an example of a form of embodiment of a facility 1 for monitoring handling of an object 4 according to the improved concept. In the present non-restrictive example, the object 4 involves a patient 4 on whom a medical procedure is being carried out by a tool 27. The tool 27 may involve a catheter 27.

The facility 1 includes a radiation source 9, for example, which may be configured to create ionizing radiation 3, (e.g., x-ray radiation 3). The facility 1 moreover includes an optical unit 2, which may include a collimator in order to parallelize the x-ray radiation of the radiation source 9 at least partly. The optical unit 2 may also include a lens arrangement and/or other optical elements, for beam forming for example.

By the optical unit 2, the x-ray radiation 3 may be directed onto the patient 4, in particular onto a region of the patient 4 at which the catheter 27 is located within the body of the patient 4. The facility 1 also includes an imaging unit 6, which in particular includes an x-ray-sensitive element, which may detect x-ray radiation 3 passing through the body of the patient 4 and, based on the x-ray radiation 3 detected, may create an image of a region of the patient 4.

The facility 1 has a visual display unit 7, (e.g., a monitor or a display), on which a representation 8 of the image may be displayed visually. To this end, image data, which includes the image, may be transmitted from the imaging unit 6 to the visual display unit 7.

An observer 25, (e.g., a doctor), who is guiding the catheter 27 in order to carry out the procedure on the patient 4, may look at the representation 8 of the image on the visual display unit 7, in particular in order to be able to carry out the guidance of the catheter 27 with x-ray assistance.

The facility moreover includes a view acquisition system, which has an eye tracker 26, for example. The eye tracker 26 may include one or more active optical sensors, in particular infrared sensors and/or include a camera system in order that viewing movements of the observer 25 and in particular a direction of view of the observer 25 may be acquired and determined. The facility 1 has a control unit 10, which is coupled in particular to the eye tracker 26 and the imaging unit 6. Moreover, the facility 1 has a processing unit 11, which is coupled to the control unit 10 and/or the eye tracker 26.

The facility 1 or the optical unit 2 further has a filter element 5, for example, an ROI filter, which may be arranged in the beam path of the x-ray radiation 3, in particular between the radiation source 9 and the patient 4. The filter element 5 attenuates an intensity of the x-ray radiation 3 in a part area of the beam path in order to keep a radiation dose as low as possible for the patient 4 and also for the observer 25. In a central area of the filter element 5, the filter element has a transparent region, (e.g., an opening), through which the x-ray radiation 3 may pass unattenuated or essentially unattenuated in order to strike a priority region 13 on the patient 4. A position of the filter element 5 and thus a position of the priority region 13 may be controlled by the control unit 10.

An image quality of the image, which may be created by the imaging unit 6, may be all the better the higher the intensity of the respective x-ray radiation 3 in the corresponding region is. In particular, a noise component in the image data reduces the higher the local x-ray intensity is. Accordingly, a particularly high image quality is able to be obtained in the priority region 13, while in the regions in which the x-ray radiation 3 is attenuated by the filter element 5, a less high image quality is able to be obtained.

Accordingly, it is advantageous to control the priority region 13 by the control unit 10 in such a way that the priority region 13 coincides where possible with an ROI 12. The ROI 12 corresponds in particular to a region of the catheter 27 that is of particular importance for the carrying out of the treatment of the patient 4. In this case, a catheter tip of the catheter 27 may be involved. The observer 25, or a further observer who is carrying out the procedure and is guiding the catheter 27 for this purpose, is observing the catheter tip for example in the image on the visual display unit 7 in order to realize a precise guidance of the catheter 27.

Therefore, the ROI 12 corresponds as a rule to a region on the patient 4 that corresponds to a direction of view or a fixation point of the observer 25 on the representation 8 of the image. The observer 25 will as a rule or for the most part be looking during the procedure at the catheter tip in the representation 8 of the image.

At run time of the facility 1, the eye tracker 26 may acquire the viewing movements of the observer 25, for example, in order to identify a position of the ROI 12 in the representation 8 and thus also on the body of the patient 4, for example, by itself or in combination with the control unit 10 and/or the processing unit 11. The eye tracker 26 may transmit view acquisition data to the control unit, and the control unit 10 may determine the position of the ROI 12 based on the view acquisition data. The position of the ROI 12 determined in this way may, in a first operating mode of the control unit 10 or of the facility 1, serve as a target position for the priority region 13. Accordingly, the control unit 10 may control the filter element 5 and thus the priority region 13 in such a way that the priority region 13 corresponds to or follows the ROI. The ROI 12 is thereby always imaged where possible with the highest possible image quality. At the same time, the overall radiation dose for the patient 4 and the observer 25 is reduced, in that, by taking into account a lower image quality outside the ROI 12, there is an attenuation of the x-ray radiation 3.

Figure 2:
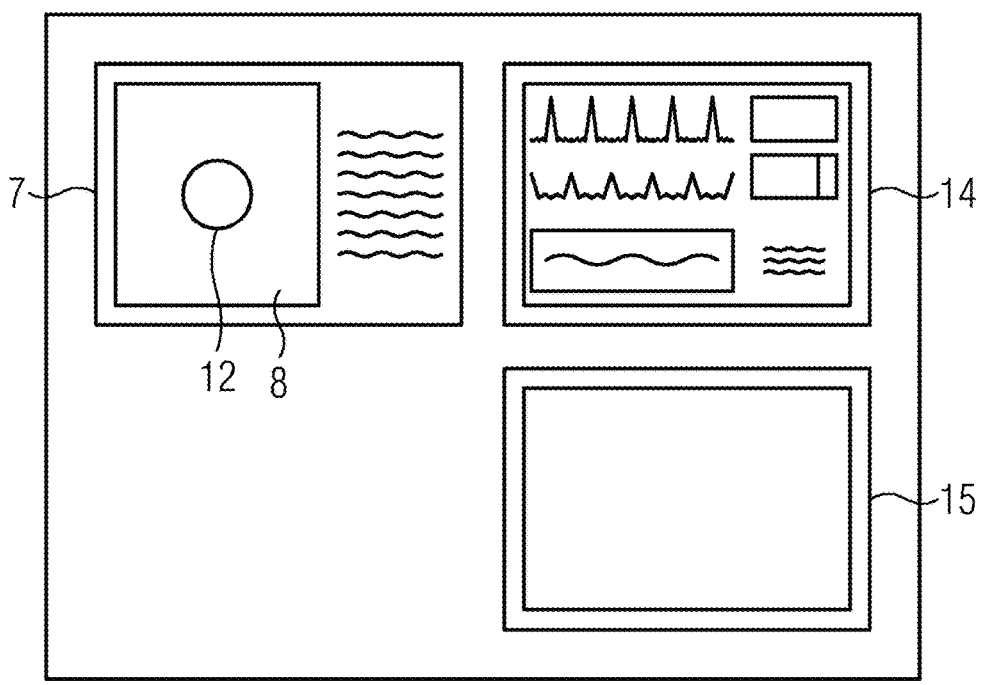
FIG. 2 depicts a schematic diagram of image display units for use with further examples of forms of embodiment of a facility according to the improved concept.

Shown once again in FIG. 2 are the visual display unit 7 with the representation 8 of the image and the ROI 12. Moreover, two further visual display units 14, 15 are shown, for example, on which further information, which may involve the handling of the patient 4, may be shown. An EKG of the patient 4, a reference image, or the like may be shown on the further visual display units 14, 15.

During the handling of the patient 4, it may occur that the observer 25 looks away from the representation 8 of the image and from the visual display unit 7, for example, in order to look at one of the further visual display units 14, 15 or directly at the patient 4 or the catheter 27.

The eye tracker 26 is in particular configured to identify one or more viewing movement sequences in the viewing movements of the observer 25, which correspond to one of the described situations, in which the observer 25 looks away from the visual display unit 7 at one of the further visual display units 14, 15 or at the catheter 27. To this end, the eye tracker 26, for example, in combination with the processing unit 11 and/or the control unit 10, may apply methods for machine learning, (e.g., artificial neural networks or K-means classifications), or conventional methods for following view trajectories.

The observer 25 may intentionally look away from the visual display unit 7 and, for example, shortly thereafter look back again at the previous location in the representation 8. The eye tracker 26 may identify, based on a relatively rapid viewing movement of the observer 25 in a predefined direction, which corresponds for example to a direction from the visual display unit 7 to one of the further visual display units 14, 15 or to the catheter 27 in order to identify the viewing movement sequences.

Optionally, the eye tracker 26 may additionally use predetermined information, for example, about the person involved as the observer 25, about the type of handling involved, which additional visual display units 14, 15 are available or how these are arranged, how a monitor layout of the visual display units 7, 14, 15 is structured, whether an EKG and/or a reference image is being used or the like in order to guarantee a more reliable recognition of the viewing movement sequences.

If one of the predetermined viewing movement sequences has been identified by the eye tracker 26, then the control unit 10 may switch itself or the facility 1 into a second operating mode. In the second operating mode, the filter element 5 and its position may no longer be controlled based on the view acquisition data of the eye tracker 26 and the target position established therefrom. Instead, the processing unit 11 is configured, based on the image data that has been created by the imaging unit 6, to carry out an image analysis in order to identify a position of the catheter tip or of another marked region of the catheter 27 and to predetermine this as the target position for the priority region 13.

The control unit 10 is configured, during the second operating mode, to control the position of the filter element 5 and thus of the priority region 13 as a function of the target position for the priority region 13 determined by the image analysis. Accordingly, even if the observer 25 is not looking at the representation 8 of the image at that moment and/or if the view of observer 25 cannot be acquired by the eye tracker 26 for this or other reasons, the position of the priority region 13 may be controlled in accordance with the presumed or apparent ROI.

In particular, the filter element 5, in such a case, e.g., in the second operating mode, is not moved completely out of the beam path of the x-ray radiation 3. Accordingly, a radiation dose for the patient 4 and the observer 25 is reduced.

A further advantage is that, as a result thereof, the filter element 5 also does not have to be moved back into the beam path of the x-ray radiation 3 when the observer 25 is again looking at the representation 8 of the image. This enables disruptions, such as image artifacts during the moving back in of the filter element 5, to be prevented.

The processing unit 11 may carry out the image analysis of the image data for example based on a model, in particular based on a trained model, in particular by employing methods for machine learning, for instance for assisted machine learning. In this case, a Bayes classifier, a naive Bayes classifier, a next neighbor classifier, a discrimination analysis, and/or an artificial neural network may be employed for supervised learning.

Figure 3:
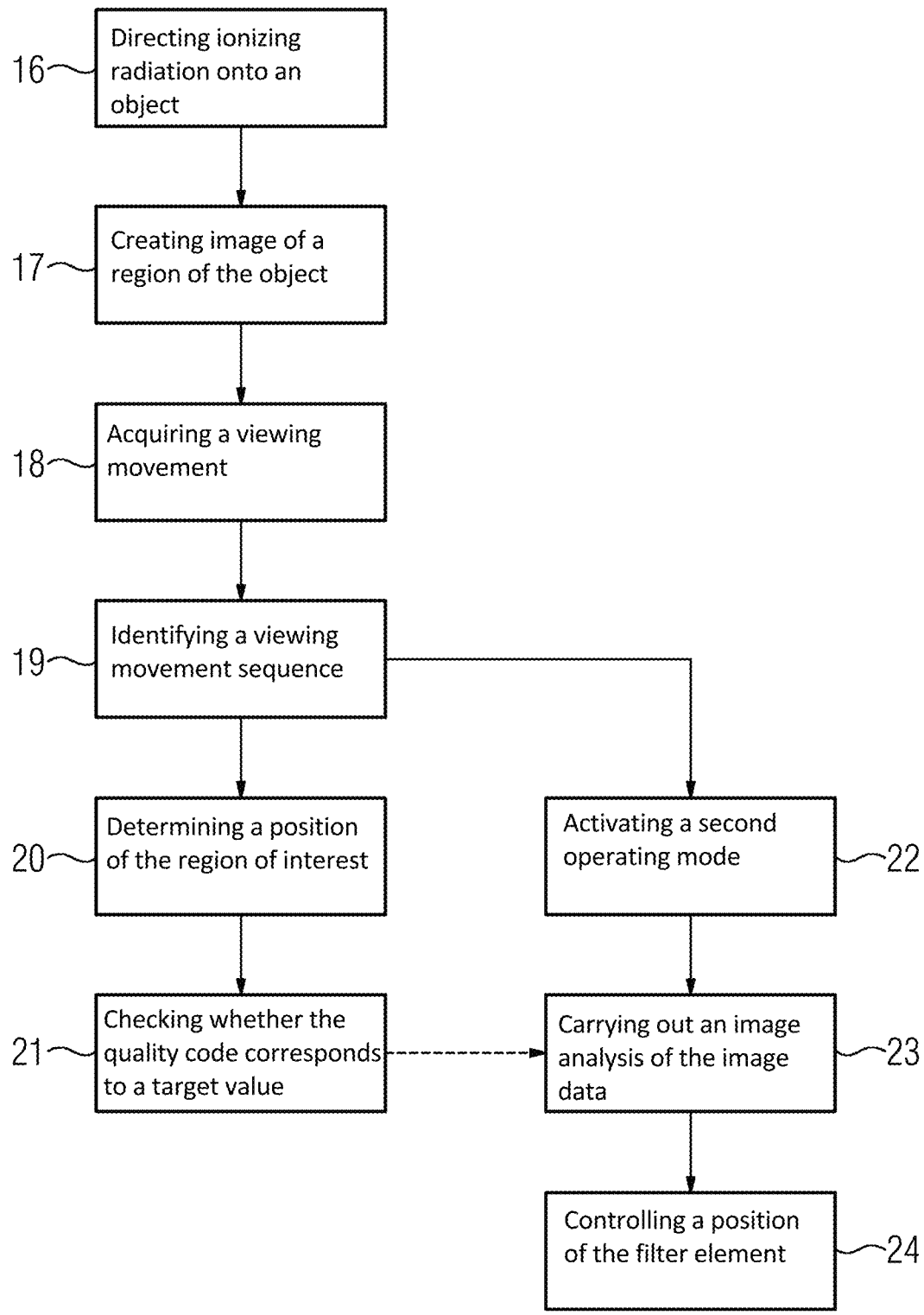
FIG. 3 depicts a flow diagram of an example of a form of embodiment of a method according to the improved concept.

Shown in FIG. 3 is an example of a form of embodiment of a method for monitoring handling of an object, for example by a facility from FIG. 1, as well as an example of a form of embodiment of a method for training a model of the image analysis according to the improved concept, in particular in the form of a flow diagram.

As regards the individual acts, the reader is also referred to what has been said in respect of FIG. 1 and FIG. 2. In act 16 of the method, the ionizing radiation 3 is directed by the radiation source 9 and the optical unit 2 as well as the filter element 5 onto the patient 4 and the part of the ionizing radiation 3 that does not pass through the opening of the filter element 5 is attenuated accordingly. In act 17, based on portions of the ionizing radiation 3 passing through the patient 4, the image of the region of the patient 4 that the radiation 3 is striking is created by the imaging unit 6.

In act 18, the viewing movement of the observer 25 is acquired, in particular by the eye tracker 26, and the position of the priority region 13 is controlled, as described with regard to FIG. 1, as a function of the viewing movements.

In act 19, one of the predefined viewing movement sequences is identified, which indicates that the view of the observer 25 is diverted away from the representation 8 of the image. Now, in act 22, the second operating mode is activated by the control unit 10.

In act 23, the processing unit 11 carries out an image analysis of the image data of the image. By the image analysis, a position of a marked region of the catheter 27, in particular of the catheter tip, is identified and set as target position for the priority region 13. In act 24, the position of the filter element 5 is controlled by the control unit 10 in such a way that the position of the priority region 13 corresponds to the target position and accordingly the catheter tip may be imaged with high quality.

The image analysis may be undertaken based on a predetermined parameter set. The parameter set may originate from a training method according to the improved concept. In particular, in act 20, the position of the ROI 12 determined by the processing unit based on the by the eye tracker 26 in the first operating mode in act 18 may be compared with the position of the catheter tip determined from the image analysis in order to adapt or update the model parameters, e.g., the parameter set, for localization of the catheter tip based on the image data.

Target positions that have been determined by the eye tracker 26 during the first operating mode are thus used as training data for the optimization or the training of the model. Based on the comparison of a position of the catheter tip, as has been computed by the model, with the position of the ROI from the view acquisition data, a quality code for the current parameter set of the model is determined. The quality code in this case quantifies a deviation between the two positions. The greater the deviation the worse is the quality of the parameter set determined.

In act 21, it is checked whether the quality code corresponds to a predetermined target value for the quality. The acts of determining the position of the catheter tip by the model, of comparing it with the ROI position from the view acquisition data and of adapting the parameter set are repeated iteratively for example, until it is established in act 21 that the quality code corresponds to a predetermined target value for the quality. If this is the case, the parameter set established in this way may be passed on to act 23 of the method at run time, and the model may be used at run time during the second operating mode in order to serve as a basis for control of the filter element 5.

The training method according to the improved concept may thus be used to advantage at least in part online, e.g., during the run time of the method, for monitoring the handling of the patient 4 and thus inherently to create the specific special features of the actual system construction as well as to take account of user-specific details in order to create the parameter set.

Figure 4:
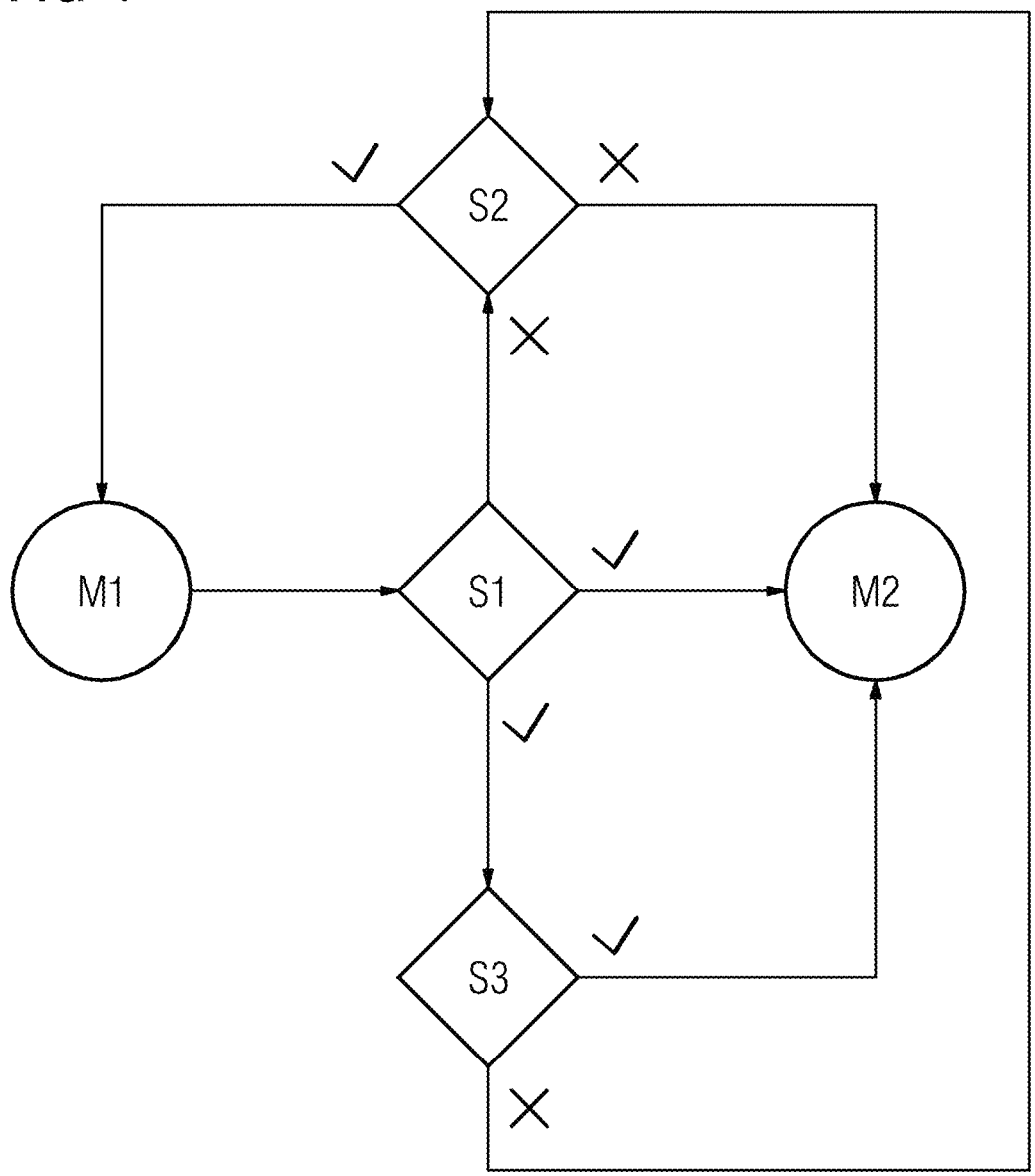
FIG. 4 depicts a further flow diagram of an example of a form of embodiment of a method according to the improved concept.

Shown in FIG. 4 is a further example of a form of embodiment of a method for monitoring handling of an object, for example by a facility from FIG. 1. As regards the individual acts, the reader is referred to what has been said in respect of FIG. 1 and FIG. 2.

In act M1, the facility 1 or the control unit 10 is operated in the first operating mode, as described in relation to FIG. 1 to FIG. 3. In particular, the viewing movement of the observer 25 is acquired by the eye tracker 26 and the position of the priority region 13, as described with regard to FIG. 1, is controlled as a function of the viewing movements.

In act S1, a check is made as to whether one of the predefined sequences of viewing movements or a further predetermined sequence of viewing movements may be identified.

The further sequence of viewing movements differs for example from the sequences of viewing movements in that, if the further sequence of viewing movements is present, it cannot necessarily be concluded that the observer 25 has only looked away briefly from the visual display unit 7 in order then to look back again at the previous location in the representation 8.

If neither one of the predefined sequences of viewing movements nor the further sequence of viewing movements is identified, then a check is made in act S2 as to whether the view of the observer 25 may still be acquired by the eye tracker 26. If this is the case, then the first operating mode is retained. Otherwise, a switch is made in act M2 into the second operating mode, is stated with regard to FIG. 1 to FIG. 3.

If, in act S1, one of the sequences of viewing movements is identified, a switch is likewise made in act M2 into the second operating mode.

If, in act S1, the further sequence of viewing movements is identified, then a check is made in act S3 as to whether a predefined status variable of the facility 1, (e.g., a SID or an angulation), is changing or has changed. If this is the case, then a switch is likewise made in act M2 into the second operating mode.

Otherwise the execution sequence continues with act S2, as stated above.

If the further sequence of viewing movements was identified and if in addition the change in the status variable is present, then it may be assumed for example that the observer 25 has only looked away briefly from the visual display unit 7.

The improved concept enables the filter element being removed from the beam path of the ionizing radiation in order to make possible a sufficiently high image quality in the priority region to be avoided in situations in which the observer may intentionally look away from the visual display unit or in which the eye tracker may no longer acquire the viewing movements of the observer for other reasons. This enables a radiation dose to be reduced for object and observer.

The filter element may remain permanently in the beam path during the second operating mode. As an alternative, the filter element may be removed completely from the beam path after a specific period of time after activation of the second operating mode if it is not detected that the observer is looking back again at the visual display unit.

Both the use of an eye tracker and also the image analysis situations may occur in which the priority region cannot be correctly positioned. According to the improved concept, these two approaches to control complement one another, so that moving the filter element out of the beam path may be avoided.

The overall effectiveness of the filter element (e.g., dose reduction) is thus increased. Moreover, disruptive artifacts are avoided for the observer through the movement of the filter element into and out of the beam path. By a training method according to the improved concept, there may be training of the image analysis model tailored specifically to the concrete situation in a method for monitoring the handling according to the improved concept. Through the eye tracker information, e.g., the view acquisition data, very good training data is available for training the model. In particular, the quality of the model may be improved during each run time.

In particular, algorithms that are based on artificial intelligence or on machine learning may be employed for training in order to optimize the control of the filter element based on the image analysis. The training may be done in particular online using the data delivered by the eye tracker. A further advantage is that the tracking of the viewing movements by the eye tracker is very accurate as a rule and correspondingly good input data is available for the training.

Although the disclosure has been illustrated and described in greater detail by the exemplary embodiments, the disclosure is not restricted by these exemplary embodiments. Other variations may be derived herefrom by the person skilled in the art, without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A facility for monitoring handling of an object, the facility comprising:
an optical unit configured to direct ionizing radiation onto the object;
a filter element configured to be arranged in a beam path of the ionizing radiation to attenuate a part of the ionizing radiation;
an imaging unit configured to detect portions of the ionizing radiation passing through the object in order to create an image of a part of the object;
a view acquisition system configured to acquire a viewing movement of an observer; and
a control unit configured, during a first operating mode, to control a position of the filter element as a function of the viewing movement,
wherein the control unit is configured to:
identify a predefined sequence of viewing movements of the observer as a function of the acquired viewing movement of the observer;
switch from the first operating mode into a second operating mode when the predefined sequence of viewing movements of the observer has been identified; and
during the second operating mode, control the position of the filter element as a function of an image analysis of the image.

2. The facility of claim 1, wherein the control unit is configured to:
detect, as a function of the viewing movement, whether a direction of view of the observer lies within a predetermined view direction area; and
retain the first operating mode or to switch from the second operating mode into the first operating mode when the direction of view lies within the view direction area.

3. The facility of claim 1, wherein, through the identification of the predefined sequence of viewing movements of the observer, the facility is configured to detect that a direction of view of the observer lies within a predetermined further view direction area.

4. The facility of claim 1, wherein the control unit is configured to switch from the first operating mode into the second operating mode when the view acquisition system cannot acquire the viewing movement of the observer.

5. The facility of claim 1, further comprising:
a processing unit configured to carry out an image analysis in order to determine a position of a region of interest,
wherein the control unit is configured to control the position of the filter element during the second operating mode as a function of the position of the region of interest.

6. The facility of claim 1, wherein the control unit is configured to:
repeatedly acquire the viewing movement and to compare the repeatedly acquired viewing movement with the predefined sequence of viewing movements of the observer; and
identify the predefined sequence of viewing movements of the observer based on a result of the comparison.

7. The facility of claim 1, wherein the control unit is configured to:
identify a predefined further sequence of viewing movements of the observer as a function of the viewing movement;
determine at least one status variable of the facility or a change in the at least one status variable; and
switch from the first operating mode into the second operating mode, depending on the at least one status variable or on the change in the at least one status variable, when the predefined further sequence of viewing movements of the observer has been identified.

8. A facility for monitoring handling of an object, the facility comprising:
an optical unit configured to direct ionizing radiation onto the object;
a filter element configured to be arranged in a beam path of the ionizing radiation to attenuate a part of the ionizing radiation;
an imaging unit configured to detect portions of the ionizing radiation passing through the object in order to create an image of a part of the object;
a view acquisition system configured to acquire a viewing movement of an observer; and
a control unit configured, during a first operating mode, to control a position of the filter element as a function of the viewing movement,
wherein the control unit is configured to:
identify a predefined sequence of viewing movements as a function of the acquired viewing movement;
switch from the first operating mode into a second operating mode when the predefined sequence of viewing movements has been identified; and
during the second operating mode, control a position of a priority region based on a model,
wherein the model has been trained as a function of control data that has been created during the first operating mode in order to control the position of the priority region as a function of the acquired viewing movement.

9. The facility of claim 8, wherein the model is configured to be trained through:
   a direction of the ionizing radiation onto the object by the optical unit;
   an attenuation of the part of the ionizing radiation by the filter element in order to define a priority region;
   a creation of the image of the part of the object by the imaging unit based on portions of the ionizing radiation passing through the object;
   an acquisition of the viewing movement of the observer by the view acquisition system;
   a determination of a target position by the control unit for the priority region as a function of the acquired viewing movement; and
   a determination of a parameter set for the model by a processing unit based on a correlation of the image with the target position.

10. A training facility for a model for image analysis when monitoring handling of an object, the training facility comprising:
    an optical unit configured to direct ionizing radiation onto the object;
    a filter element configured to be arranged in a beam path of the ionizing radiation in order to attenuate a part of the ionizing radiation and thereby to define a priority region;
    an imaging unit configured to detect portions of the ionizing radiation passing through the object in order to create an image of a part of the object;
    a view acquisition system configured to acquire a viewing movement of an observer;
    a control unit configured to determine a target position for the priority region as a function of the viewing movement; and
    a processing unit configured to:
      determine a parameter set for the model based on a correlation of the image with the target position;
      determine a further target position for the priority region based on the model using the parameter set determined based on the image;
      compare the further target position with the target position; and
      determine a quality code for the parameter set defined based on a result of the comparison.

11. A method for training a model for image analysis when monitoring handling of an object, the method comprising:
    directing, by an optical unit, ionizing radiation onto the object;
    attenuating, by a filter element, a part of the ionizing radiation in order to define a priority region;
    creating, by an imaging unit, an image of a part of the object based on portions of the ionizing radiation passing through the object;
    acquiring, by a view acquisition system, a viewing movement of an observer;
    determining, by a control unit, a target position for the priority region as a function of the viewing movement;
    determining, by a processing unit, a parameter set for the model based on a correlation of the image with the target position;
    determining, by the processing unit, a further target position for the priority region based on the model using the parameter set determined based on the image;
    comparing, by the processing unit, the further target position with the target position; and
    determining, by the processing unit, a quality code for the parameter set defined based on a result of the comparing.

12. A method for monitoring handling of an object, the method comprising:
    directing, by an optical unit, ionizing radiation onto the object;
    attenuating, by a filter element, a part of the ionizing radiation in order to define a priority region;
    creating, by an imaging unit, an image of a part of the object based on portions of the ionizing radiation passing through the object;
    acquiring, by a view acquisition system, a viewing movement of an observer;
    controlling, by a control unit during a first operating mode, a position of the priority region as a function of the acquired viewing movement of the observer;
    identifying, by the control unit, a predefined sequence of viewing movements of the observer as a function of the acquired viewing movement of the observer;
    switching, by the control unit, from the first operating mode into a second operating mode when the predefined sequence of viewing movements of the observer has been identified; and
    controlling, by the control unit during the second operating mode, the position of the priority region as a function of an image analysis of the image.

13. The method of claim 12, further comprising:
    determining a target position for the priority region to control the position of the priority region as a function of the viewing movement; and
    controlling a position of a filter element for attenuating the part of the radiation such that the position of the priority region matches the target position.

14. The method of claim 13, wherein the position of the priority region is controlled during the second operating mode based on a model, and
    wherein the model is trained as a function of control data created during the first operating mode in order to control the position of the priority region as a function of the acquired viewing movement of the observer.

15. The method of claim 14, wherein the model is trained by:
    directing, by the optical unit, the ionizing radiation onto the object;
    attenuating, by the filter element, the part of the ionizing radiation in order to define the priority region;
    creating, by the imaging unit, the image of the part of the object based on the portions of the ionizing radiation passing through the object;
    acquiring, by the view acquisition system, the viewing movement of the observer;
    determining, by the control unit, the target position for the priority region as a function of the viewing movement; and
    determining, by a processing unit, a parameter set for the model based on a correlation of the image with the target position.

16. The method of claim 12, further comprising:
    determining, by a processing unit, a position of a region of interest through the image analysis; and
    defining, by the processing unit, the position of the region of interest as a further target position for the priority region in order to control the position of the priority region during the second operating mode.

\* \* \* \* \*